(12) United States Patent
Wurth

(10) Patent No.: US 11,744,742 B1
(45) Date of Patent: Sep. 5, 2023

(54) CRYOTHERAPY DRESSING SYSTEM

(71) Applicant: Todd R. Wurth, Brentwood, TN (US)

(72) Inventor: Todd R. Wurth, Brentwood, TN (US)

(*) Notice: Subject to any disclaimer, the term of this patent is extended or adjusted under 35 U.S.C. 154(b) by 409 days.

(21) Appl. No.: 16/898,245

(22) Filed: Jun. 10, 2020

Related U.S. Application Data

(60) Provisional application No. 62/859,224, filed on Jun. 10, 2019.

(51) Int. Cl.
*A61F 13/02* (2006.01)
*A61F 13/04* (2006.01)
*A61M 1/00* (2006.01)

(52) U.S. Cl.
CPC ........ *A61F 13/0216* (2013.01); *A61F 13/046* (2013.01); *A61M 1/74* (2021.05); *A61M 1/962* (2021.05); *A61M 2205/3606* (2013.01)

(58) Field of Classification Search
CPC .. A61F 13/046; A61F 7/00; A61F 7/02; A61F 2007/0054; A61F 2007/0063; A61F 2007/0069
See application file for complete search history.

(56) References Cited

U.S. PATENT DOCUMENTS

| | | | | |
|---|---|---|---|---|
| 4,621,624 A * | 11/1986 | Rayboy | ................ | A61F 13/046 607/104 |
| 5,072,875 A * | 12/1991 | Zacoi | ....................... | A61F 7/02 607/104 |
| 5,080,089 A * | 1/1992 | Mason | ..................... | A61F 7/00 607/104 |
| 5,314,455 A | 5/1994 | Johhson, Jr. et al. | | |
| 6,117,164 A * | 9/2000 | Gildersleeve | ............. | A61F 7/02 607/108 |
| 6,508,831 B1 * | 1/2003 | Kushnir | .................... | A61F 7/00 607/104 |
| 7,144,390 B1 * | 12/2006 | Hannigan | ................. | A61F 7/10 601/7 |
| 7,615,036 B2 | 11/2009 | Joshi et al. | | |
| 8,920,830 B2 | 12/2014 | Mathies | | |
| 2007/0000278 A1 * | 1/2007 | Collins | ..................... | A61F 7/12 62/434 |
| 2011/0098793 A1 * | 4/2011 | Lowe | .................... | A61F 7/0085 607/104 |
| 2012/0220960 A1 * | 8/2012 | Ruland | ..................... | A61F 7/02 604/291 |
| 2013/0165821 A1 | 6/2013 | Freedman et al. | | |

FOREIGN PATENT DOCUMENTS

| | | |
|---|---|---|
| WO | 2004/052414 A1 | 6/2004 |
| WO | 2007/041642 A2 | 4/2007 |
| WO | 2016/034752 A1 | 3/2016 |

* cited by examiner

*Primary Examiner* — Catharine L Anderson
*Assistant Examiner* — Arjuna P Chatrathi
(74) *Attorney, Agent, or Firm* — Alexandra C. Lynn; Timothy L. Capria

(57) ABSTRACT

A dressing system for cooling skin or a wound site on a subject comprises a dressing having a reservoir for holding a liquid. The dressing may be configured for placement proximate to a postoperative surgical wound site of the subject or on the facial area of the subject. The dressing system includes a cooling chamber external to the dressing configured to cool the liquid. The dressing system includes a pump configured to circulate the liquid between the cooling chamber and the reservoir. The dressing system may include a suction element for applying suction at, or proximate to, the dressing for removing sweat or wound drainage.

21 Claims, 5 Drawing Sheets

CRYOTHERAPY DRESSING SYSTEM

CROSS-REFERENCE TO RELATED APPLICATION(S)

This application claims the benefit of U.S. Provisional Patent Application No. 62/859,224, filed Jun. 10, 2020, which is incorporated by reference herein in its entirety.

TECHNICAL FIELD

The present disclosure relates to a dressing system. More specifically, the disclosure is directed towards a cryotherapy dressing system including a dressing actively cooled by a cooled liquid, the cooled liquid circulated through the system by a pump and cooled by coolant. The dressing system may also include a suction element for applying suction at, or proximate to, the dressing.

BACKGROUND OF INVENTION

Wound care is a critical aspect of healing and surgery. Indeed, in 2016, the global wound care market was valued at approximately $23.3 billion and is estimated to significantly grow. While promoting fast and complete wound care is important on the one hand, these considerations must be weighed against and balanced with subject comfort and pain management. Subject pain management is especially relevant in the present clinical environment of minimizing prescribed narcotic use. What are needed, then, are systems and methods for effectively promoting healing in wounds that are comfortable for the subject and reduce subject postoperative pain.

BRIEF SUMMARY

In one aspect, a dressing system for cooling skin or a wound site on a subject is disclosed. The dressing system comprises a dressing having a reservoir. The dressing may be configured for placement proximate to a postoperative surgical wound site of the subject. The postoperative surgical wound site may be, for example, a postoperative splint, within a postoperative dressing, within cast padding under a cast. The dressing may comprise a supplemental dressing configured for use with a primary dressing. The dressing may be constructed of a pliable material.

The dressing system comprises a cooling chamber external to the dressing. Coolant, such as ice, may be disposed at least partially around the cooling chamber.

The dressing system comprises a pump configured to circulate a liquid between the cooling chamber and the reservoir of the dressing. The pump may be configured to move liquid from the cooling chamber to the reservoir through a coolant hose and the liquid from the reservoir to the cooling chamber through a return hose. The liquid may comprise water or saline and may be sterile.

The dressing system may include a suction element for removing wound drainage or sweat from the area proximate to the dressing. The dressing system may have a drain cavity for receiving and storing the wound drainage or sweat and a drain hose in fluid communication with the suction element for moving the wound drainage or sweat from the suction element to the drain cavity. The pump may be configured to create the suction to the suction element through the drain hose.

The dressing system may comprise a body external to the dressing. One or more of the cooling chamber, the drain cavity, the coolant, or the pump may be disposed on the body.

In another aspect, a method of promoting healing in a subject is disclosed. The method of promoting healing in the subject comprises circulating chilled liquid from the cooling chamber to the reservoir of the dressing, the dressing positioned at, or proximate to, skin of the subject. The skin of the subject may comprise a wound site or facial skin.

In an aspect, a method of cooling a skin site of a subject is disclosed. The method comprises circulating chilled liquid from the cooling chamber to the reservoir of the dressing, the dressing positioned at, or proximate to, skin of the subject. The method may include applying negative pressure at, or proximate to, the dressing to remove wound drainage or sweat.

In yet another aspect, a method of rejuvenating facial skin is disclosed. The method comprises circulating chilled liquid from the cooling chamber to the reservoir of the dressing, the dressing positioned at, or proximate to, the facial skin of the subject. The method may include applying negative pressure at, or proximate to, the dressing.

BRIEF DESCRIPTION OF DRAWINGS

It should be noted that identical features in different drawings are shown with the same reference numeral.

DETAILED DESCRIPTION

Figure 1:
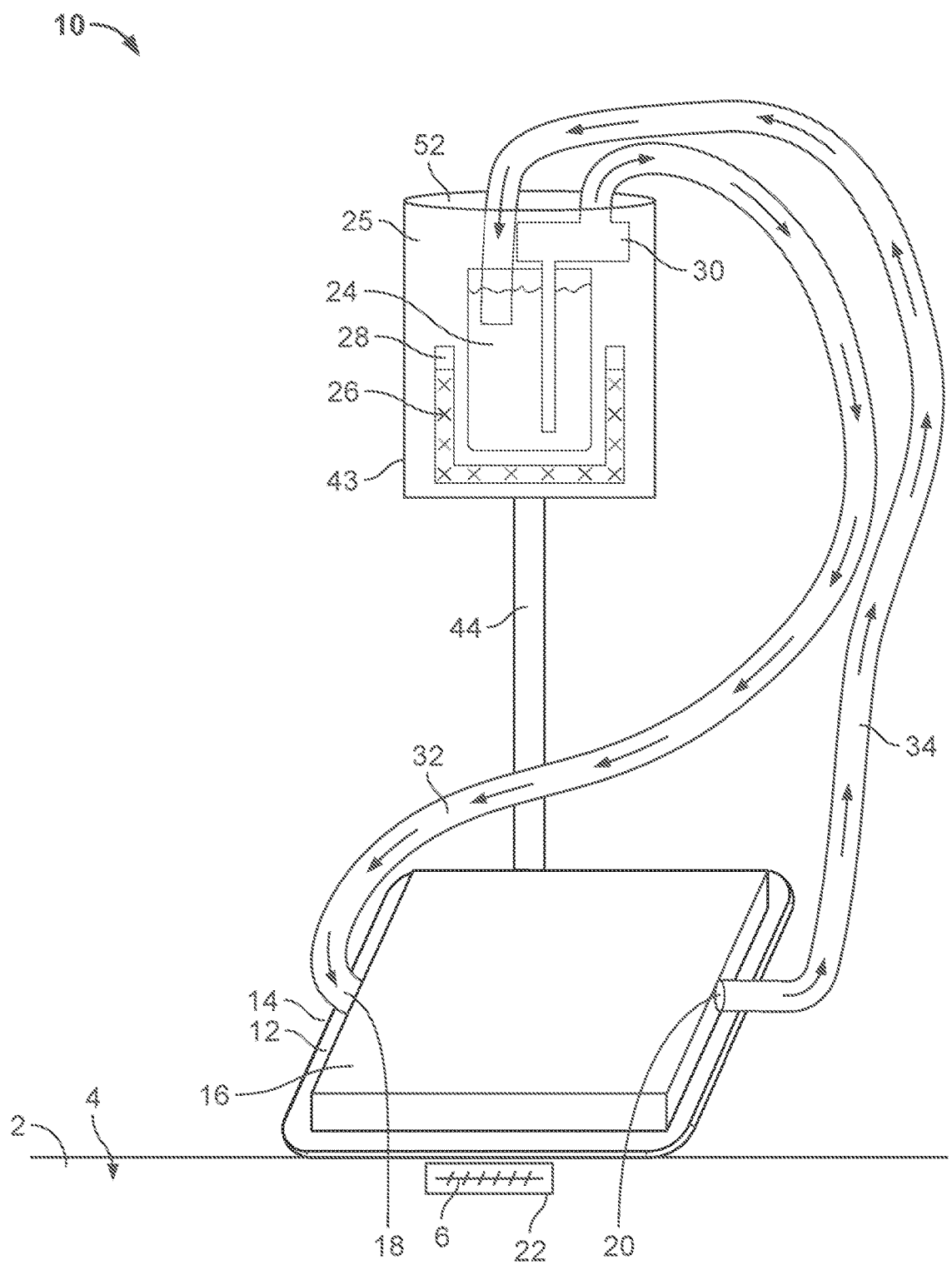
FIG. 1 is a schematic view of an embodiment of the dressing system.

Reference now will be made in detail to the embodiments of the present disclosure. It will be apparent to those of ordinary skill in the art that various modifications and variations can be made to the teachings of the present disclosure without departing from the scope of the disclosure. For instance, features illustrated or described as part of one embodiment can be used with another embodiment to yield a further embodiment.

Thus, it is intended that the present disclosure covers such modifications and variations as come within the scope of the appended claims and their equivalents. Other objects, features, and aspects of the present disclosure are disclosed in or are apparent from the following description. It is to be understood by one of ordinary skill in the art that the present disclosure is a description of exemplary embodiments only and is not intended as limited to the broader aspects of the present disclosure.

For the sake of clarity, not all reference numerals are necessarily present in each drawing figure. In addition, positional terms such as "upper," "lower," "side," "top," "bottom," "vertical," "horizontal," etc. refer to the system when in the orientation shown in the drawings. The skilled artisan will recognize that the system can assume different orientations when in use.

Systems, and methods of using, dressing systems have been developed. The systems and methods are intended to allow convenient and safe cooling and/or suction of a local site of a subject to, for example, promote wound healing or rejuvenate skin.

Referring now to the dressing system 10 of FIGS. 1-5, a dressing system 10 for cooling skin 4 or a wound site 6 on a subject 2 includes a dressing 12. The subject 2 may be any animal, including a human. The dressing 12 may comprise a removable dressing cover 14 disposed around the dressing 12. The removable dressing cover 14 may be removed or replaced, for example, between uses and between subjects, such as for cleaning of the dressing cover 14 or the dressing 12. The dressing 12 and the dressing cover 14 may each be constructed of any suitable material, such as a fabric (e.g., cotton or polyester), a polymer such as PVC, polyethylene, polyurethane), or latex.

The dressing 12 includes a reservoir 16, or a bladder, configured to receive and hold a liquid. The reservoir 16 may include a reservoir inlet 18 and a reservoir outlet 20 for receiving the liquid into and out, respectively, of the reservoir 16. The reservoir inlet 18 and the reservoir outlet 20 may each be in fluid communication with the reservoir such that the liquid may move between the inlet 18 and the outlet 20 and the reservoir 16. The reservoir 16 may be sealed and impermeable to the liquid except for the reservoir inlet 18 and the reservoir outlet 20. The reservoir 16 may also be impermeable to external liquids except as through the reservoir inlet 18 and the reservoir outlet 20. Advantageously, sealed reservoir 16 prevents the liquid from escaping onto the subject 2 when the dressing 12 is in use on the subject 2, and creates a "closed" dressing system 10. The reservoir 16 may have walls constructed of any suitable material, such as a polymer (e.g., Low Density Polyethylene (LDPE)).

The dressing 12 may be configured for placement proximate to the postoperative site 6, such as a postoperative surgical wound site, such as a postoperative splint, within a postoperative dressing, within cast padding under a cast, of the subject 2. In some embodiments, the dressing 12 is a supplemental dressing 12 for use with a primary dressing 22 that is in direct contact with the subject 2, and the dressing 12 (and/or the dressing cover 14) is in indirect contact with the subject 2 in at least one area, if not the across the entire dressing 12 and/or dressing cover 14). The dressing 12, and the dressing cover 14, may be elastic, flexible, and/or self-adhesive such that it may be used on the subject 2, for example, within cast padding worn by the subject 2.

The dressing system 10 comprises a cooling chamber 24 external to the dressing 12. The cooling chamber 24 may be disposed within a cooling chamber body 25, the body 25 constructed of any suitable material. "External" means that the cooling chamber is a discrete from, and not included on, the dressing 12. In some embodiments, "external" refers to the cooling chamber 24 not being worn by the subject. A coolant 26, such as ice or a pre-cooled refrigerant pack, may be in contact (whether directly or indirectly) with the cooling chamber 24 to cool the liquid within the chamber 24. The coolant 26 may be disposed, for example, around at least part of the cooling chamber 24. The coolant 26 may be disposed within a coolant cavity 28. In some embodiments, a cooling unit 68, such as a thermoelectric cooler or a heat exchanger, may be used to cool the liquid within the chamber 24.

The dressing system 10 may comprise a pump 30. The pump may be configured to circulate the liquid between the cooling chamber 24 and the reservoir 16 of the dressing 12. The pump 30 may be configured to move the liquid from the cooling chamber 24 to the reservoir 16 through a coolant hose 32 and the liquid from the reservoir 16 to the cooling chamber 24 through a return hose 34 in a loop. The pump 30 may be operable continuously, intermittently, via a timer, or in variable flow rates (e.g., at least one flow speeds, at least two flow speeds, at least three flow speeds, etc.). In some embodiments, a thermometer 60 is disposed on the dressing 12 and is in communication with a control unit 62 configured to selectively operate the pump 30. The control unit 62 may cause the pump 30 to operate when an initial threshold temperature is met and read by the thermometer 60. By way of example, if the initial threshold temperature is 90 degrees F., once the control unit 62 reads the temperature being above 90 degrees, F, the control unit 62 could cause the pump 30 to operate, thereby circulating the liquid and cooling the skin 4. Once the thermometer reads a certain subsequent threshold temperature, such as 40 degrees F., the control unit 62 may cause the turn off the pump 30. The control unit 62 may cause the pump 30 to operate at variable speeds based on one or more threshold temperatures (e.g., a low pump speed at a cold threshold temperature, a moderate pump speed at a warm threshold temperature, a high pump speed at a hot threshold temperature). The control unit 62 may communicate with the pump 30 and the thermometer wiredly or wirelessly. The control unit 62 (along with pumps 30, 42 and cavity 38) may be disposed on or within any suitable component of the system 10, such as within the cooling chamber body 25. The control unit may operatively and selectively control the cooling unit 68. A power supply 64 (whether AC or DC, such as a battery) may power the pumps 30, 42, and the control unit 62, and the cooling unit 68.

The liquid may comprise, for example, refrigerant, water, or saline, and may be sterile or non-sterile. Non-sterile liquid may be advantageous for personal use where sterile conditions are not important or practicable. Sterile liquid may be advantageous for medical settings, such as in clinical care settings.

Figure 2:
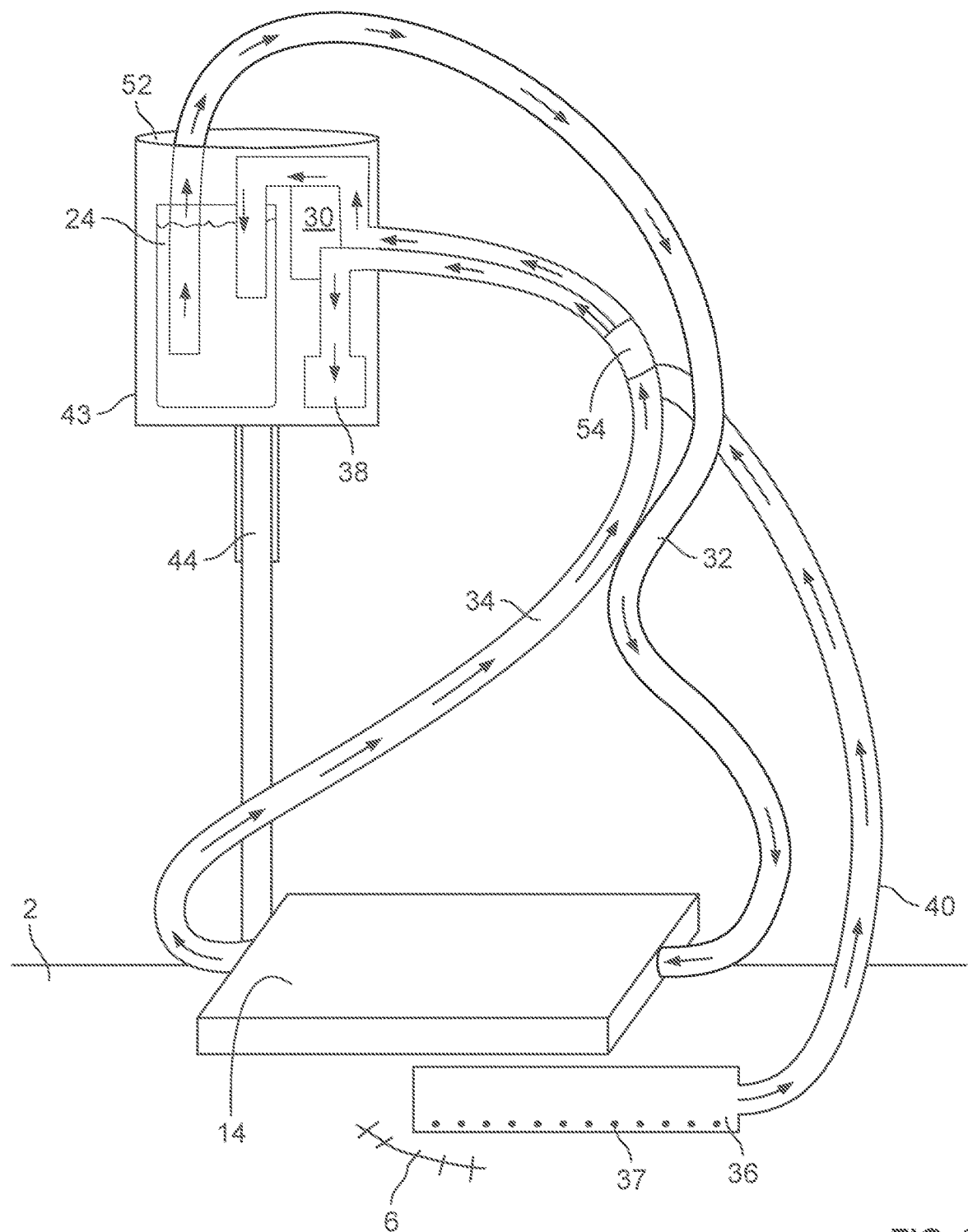
FIG. 2 is a schematic view of another embodiment of the dressing system.
Figure 3:
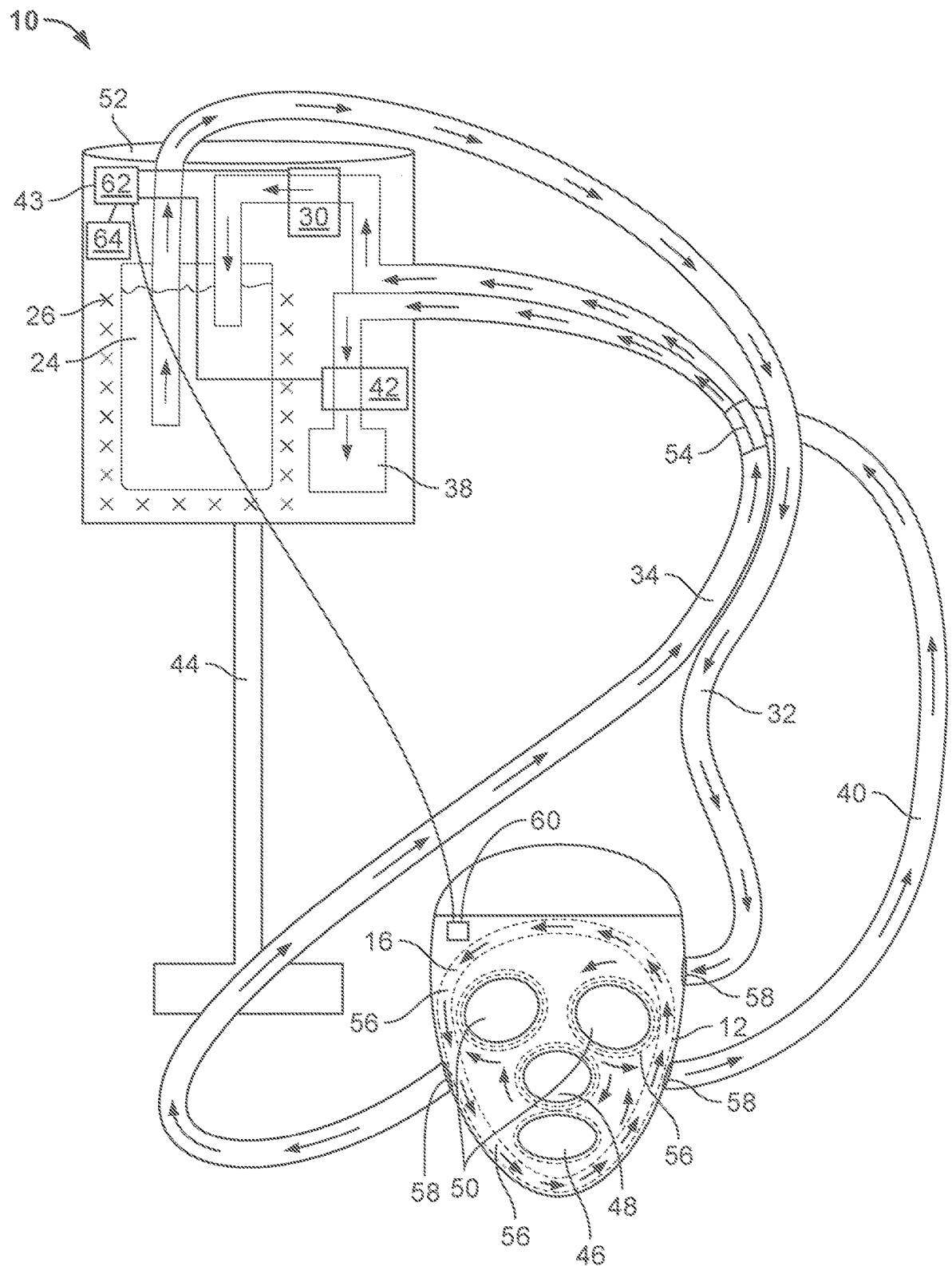
FIG. 3 is a schematic view of yet another embodiment of the dressing system.

As shown in FIG. 2, the dressing system 10 may include a suction element 36 (e.g., a drain) for removing wound drainage or sweat from the area proximate to the dressing 10. The dressing system 10 may have a drain cavity 38 for receiving and storing the wound drainage or sweat and a drain hose 40 in fluid communication with the suction element 36 for moving the wound drainage or sweat from the suction element 36 to the drain cavity 38. A second pump 42 may be configured to create the suction to the suction element 36 through the drain hose 40. The suction element 36 may include one or more suction holes 37 through which suction is applied from the second pump 42 through the drain hose 40 to the area proximate to the dressing 12. The one or more suction holes 37 may be disposed in the dressing 12 or in the dressing 12 and the cover 14. In some embodiments, the single pump 30 is used to operate both the suction element 36 and circulate the liquid. The suction holes 37 may be positioned on the dressing 12 such that the suction holes 37 generally face the skin 4 of the subject 2 such that they pull drainage from the skin 4 of the subject (or dressing area surrounding the skin 4). The suction element 36 may be provided as a discrete element (as shown in FIG. 2) or as part of the dressing 12 (as shown in FIGS. 3-5).

In some embodiments, the suction pump 42 may be used to create suction with drain hose 40 and return hose 34 while the liquid pump 30 may be used to circulate the liquid. This multi-pump configuration may be beneficial to, for example, maintain separation of sweat and wound drainage from the liquid. In some embodiments, a valve 54 (e.g., a bivalve and/or a check valve) may be used to modulate, and separate, suction from the pump 42 to the drain hose 40 and/or the return hose 34, or to ensure a one-way flow through the hoses 32, 34, 40.

The dressing system 10 may comprise a body 43 external to the dressing 12. The body 43 may be, for example, disposed on a medical cart 44 (e.g., a medical stand), located proximate to the subject 2. One or more of the cooling chamber 24, the drain cavity 38, the coolant 26, or the pump 30 may be disposed on or in the body 43. The body 43 may be constructed of any suitable material, such as metal or a polymer (whether rigid or flexible). The body 43 being external to the dressing 12 is particularly advantageous, as it enables the dressing 12 to be compact and comfortable for the subject to wear 2. The coolant 26 may be replaced by, for example, removing and adding the coolant 26 by accessing the coolant 26 through a resealable open top 52 on the body 43. The top 52 may provide access to the coolant cavity 28 for replacing the coolant 26.

The dressing system 10 may comprise a body 42 external to the dressing 12. The body 42 may be, for example, disposed on a medical cart 44 (e.g., a medical stand), located proximate to the subject 2. One or more of the cooling chamber 24, the drain cavity 38, the coolant 26, or the pump 30 may be disposed on or in the body 42. The body 42 may be constructed of any suitable material, such as metal or a polymer (whether rigid or flexible). The body 42 being external to the dressing 12 is particularly advantageous, as it enables the dressing 12 to be compact and comfortable for the subject to wear 2. The coolant 26 may be replaced by, for example, removing and adding the coolant 26 by accessing the coolant 26 through a resealable open top 52 on the body 42. The top 52 may provide access to the coolant cavity 28 for replacing the coolant 26.

Figure 4A:
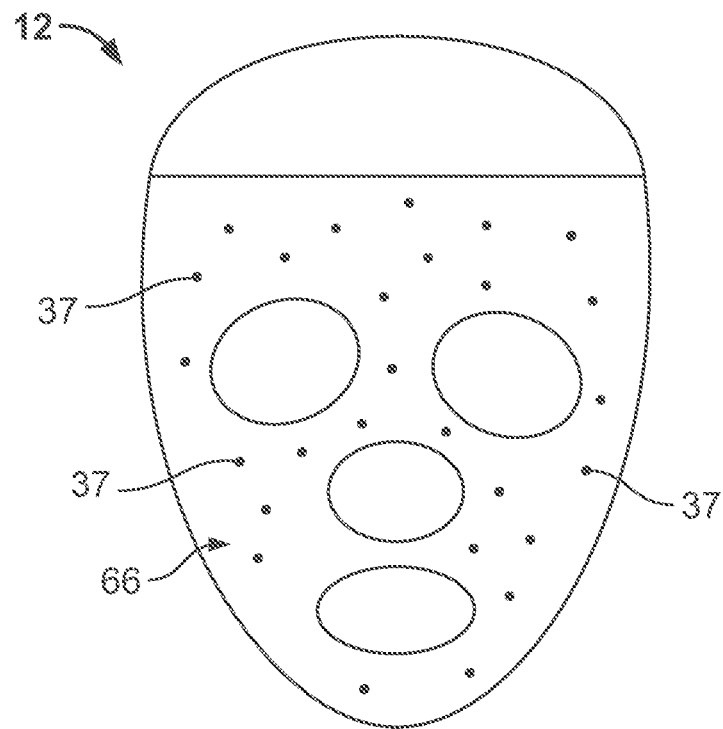
FIG. 4A illustrates a close-up bottom view of a dressing according to one embodiment of the dressing system.
Figure 4B:
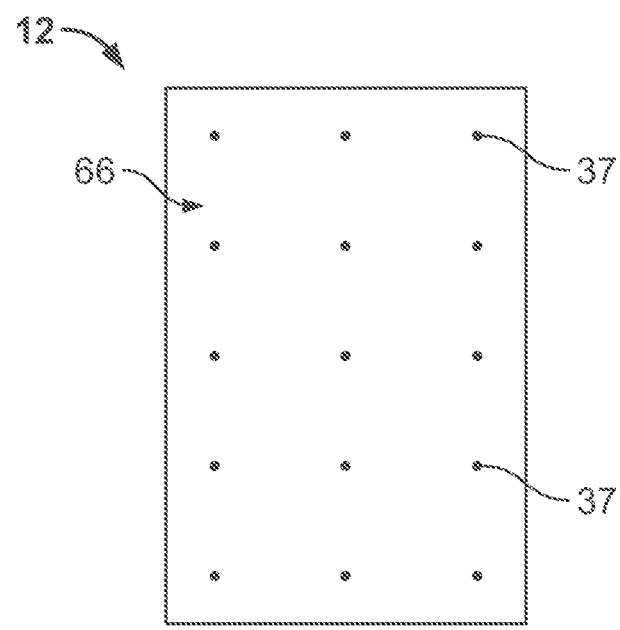
FIG. 4B illustrates a close-up bottom view of a dressing according to another embodiment of the dressing system.
Figure 5:
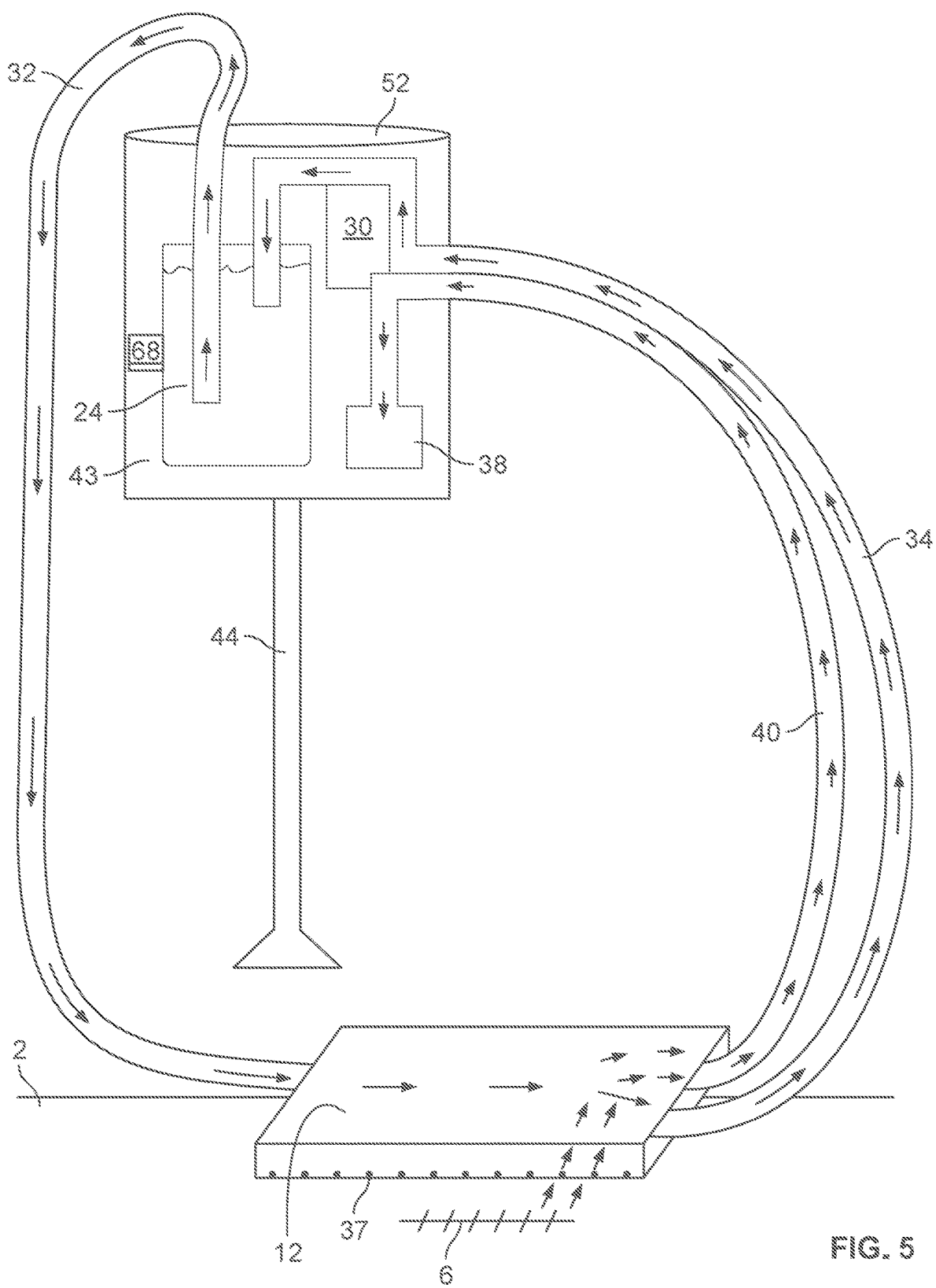
FIG. 5 is a schematic view of an embodiment of the dressing system.

As shown in FIGS. 3 and 4A, the dressing 12 may be dimensioned and shaped to be cooperatively received on a face of the subject 2. The suction element 36 may be disposed on or in the dressing 12. Advantageously, when the dressing 12 (using suction of the suction element 36 and/or cooling of the circulating coolant 26) is used in the face of the subject 2, the dressing 12 promotes epidermal and dermal health and rejuvenation (e.g., a youthful appearance). The dressing 12 may have one or more of a mouth aperture 46, a nose aperture 48, or eye aperture(s) 50.

As shown in FIGS. 4-5, the dressing 12 may include the suction element 36, including the one or more suction holes 37 disposed on a skin surface 66 (i.e., the surface of the dressing 12 that faces or is in contact with the skin 4 or the wound site 6). The one or more suction holes 37 may be in fluid or gaseous communication with the pump 30, 42 through one or more internal channels (not shown) that to allow air and liquid movement to be pumped into the holes 37, through the drain hose 40, and into the drain cavity 38.

It is believed that the suction and/or cooling decreases blood flow to soft tissues, thereby lowering inflammation, lowering edema, limiting scaring, evacuating wound dressing, and promoting faster wound healing and recovery in postoperative applications (e.g., after facial cosmetic surgery). Moreover, the dressing 12 may have beneficial effects for facial skin care and rejuvenation, regardless of whether the subject 2 has a postoperative surgical wound.

As can be seen in FIG. 3, the dressing 12 may have a low profile design and be constructed of a soft and pliable material. This design is especially advantageous in facial applications, as eliminating or reducing sharp folds and having a profile that is shaped to contour a face prevents skin irritation. Using the features described herein, the dressing system 10 may be varied to include a dressing 12 that has a site-specific profile for use in, for example, plastic surgery, neurosurgery, urological surgery, ENT surgery, maxillofacial surgery, orthopedic surgery, and general surgery. That is, the dressing 12 may have a cooperative profile with the site-specific area on the subject 2 that is desired to be cooled and/or suctioned (e.g., neck, top or crown of head, nose, etc.) such that the dressing 12 can be worn on the subject 2 without folds or wrinkles in the dressing 12. This site-specific profile feature is believed to add to the healing and rejuvenating attributes of the dressing system 10.

Embodiments of the dressing system 10 described herein may be used in methods of promoting healing in a subject, such as promoting healing of the skin 4 of the subject. The method includes circulating the liquid from the cooling chamber 24 to the reservoir 16 of the dressing 12, the dressing 12 positioned at, or proximate to, the skin 4 of the subject 2. The skin 4 of the subject 2 may comprise a wound site 6, facial skin 4, or both. The method may include applying negative pressure at, or proximate to, the dressing 12, such as via suction element 36. The method may include suctioning and capturing wound drainage or sweat.

Embodiments of the dressing system 10 described herein may be used in methods of rejuvenating facial skin 4. The method includes circulating the liquid from the cooling chamber 24 to the reservoir 16 of the dressing 12, the dressing 12 positioned at, or proximate to, facial skin 4 of the subject 2. The method may include applying negative pressure at, or proximate to, the dressing 12, such as via suction element 36. The method may include suctioning and capturing wound drainage or sweat.

Embodiments of the dressing system 10 described herein may be used in methods of cooling and/or applying negative pressure to the skin 4 of the subject 2. The method includes circulating the liquid from the cooling chamber 24 to the reservoir 16 of the dressing 12, the dressing 12 positioned at, or proximate to, the skin 4 of the subject 2. The method may include applying negative pressure at, or proximate to, the dressing 12, such as via suction element 36. The method may include suctioning and capturing wound drainage or sweat. Also advantageously, the cooling and/or suction features of the present dressing system 10 reduce, or eliminate, postoperative pain.

Although embodiments of the disclosure have been described using specific terms, devices, and methods, such description is for illustrative purposes only. The words are words of description rather than of limitation. It is to be understood that changes and variations may be made by those of ordinary skill in the art without departing from the spirit or scope of the present disclosure, which is set forth in the following claims. It is further noted that any range provided herein provides support and a basis for any subset within that range. Further embodiments of the disclosure contain combinations, or exclusions, of different embodiments described herein.

Thus, although there have been described particular embodiments of the present invention of a new and useful dressing system, it is not intended that such references be construed as limitations upon the scope of this invention except as set forth in the following claims.

What is claimed is:

1. A dressing system, comprising:
a dressing including a reservoir;
a cooling chamber external to the dressing;
a coolant disposed at least partially around the cooling chamber;
a cooled liquid;

a cooled liquid hose for circulating the cooled liquid between the cooling chamber and the reservoir of the dressing;
a suction element for providing negative pressure at the dressing;
a drain cavity;
a drain hose for moving material suctioned from the suction element to the drain cavity, wherein the material is kept separate from the cooled liquid;
a pump configured to circulate the cooled liquid between the cooling chamber and the reservoir of the dressing and configured to create suction to the suction element to the drain hose; and
a pump valve for modulating suction to the drain hose and to the cooling hose.

2. The dressing system of claim 1, wherein the dressing comprises a face mask with at least one eye aperture, a nose aperture, and a mouth aperture, and wherein the reservoir of the face mask includes internal passageways encircling each of the apertures, the internal passageways in fluid communication with the cooling chamber, such that the cooled liquid circulates through the internal passageways in the face mask.

3. The dressing system of claim 1, further comprising a return hose in fluid communication with the reservoir and the cooling chamber.

4. The dressing system of claim 3, wherein the pump is configured to move the liquid from the cooling chamber to the reservoir through the cooled liquid hose, and wherein the pump is configured to move the liquid from the reservoir to the cooling chamber through the return hose.

5. The dressing system of claim 1, wherein the dressing is configured for placement proximate to a postoperative surgical site of a subject.

6. The dressing system of claim 5, wherein the postoperative surgical site comprises under a postoperative splint, within a postoperative dressing, or within cast padding under a cast.

7. The dressing system of claim 1, wherein the dressing is constructed of a pliable material.

8. The dressing system of claim 1, wherein the dressing is a supplemental dressing configured for use with a primary dressing.

9. The dressing system of claim 1, wherein the coolant comprises ice.

10. The dressing system of claim 1, wherein the liquid comprises water or saline.

11. The dressing system of claim 1, wherein the liquid is sterile.

12. The dressing system of claim 1, further comprising a control unit, the control unit configured to operate the pump at variable flow rates.

13. The dressing system of claim 1, wherein the suction element is configured to vacuum wound drainage or sweat from an area on a subject at, or proximate to, the dressing through the drain hose to the drain cavity.

14. The dressing system of claim 12, wherein a thermometer is disposed on the dressing, the thermometer in connection with the control unit, and wherein the control unit is configured to operate at variable speeds based on one or more threshold temperatures identified by the thermometer.

15. The dressing system of claim 1, further comprising a body external to the dressing, wherein the cooling chamber and the drain cavity are disposed within the body.

16. A method of promoting healing in a subject, the method comprising:
placing a dressing system at, or proximate to, skin of the subject, the dressing system including:
a dressing including a reservoir;
a cooling chamber external to the dressing;
a cooled liquid;
a cooled liquid hose for circulating the cooled liquid between the cooling chamber and the reservoir of the dressing;
a suction element for providing negative pressure at the dressing;
a drain cavity;
a drain hose for moving material suctioned from the suction element to the drain cavity, wherein the material is kept separate from the cooled liquid;
a pump configured to circulate the cooled liquid between the cooling chamber and the reservoir of the dressing and configured to create suction to the suction element to the drain hose; and
a pump valve for modulating suction to the drain hose and to the cooling hose, and
circulating the chilled liquid from the cooling chamber to the reservoir of the dressing.

17. The method of claim 16, wherein the skin comprises a wound site or facial skin.

18. The method of claim 16, further comprising applying negative pressure at, or proximate to, the dressing to remove wound drainage or sweat.

19. A method of cooling a skin site of a subject, the method comprising:
placing a dressing system at, or proximate to, skin of the subject, the dressing system including:
a dressing including a reservoir;
a cooling chamber external to the dressing;
a coolant disposed at least partially around the cooling chamber;
a cooled liquid;
a cooled liquid hose for circulating the cooled liquid between the cooling chamber and the reservoir of the dressing;
a suction element for providing negative pressure at the dressing;
a drain cavity;
a drain hose for moving material suctioned from the suction element to the drain cavity, wherein the material is kept separate from the cooled liquid;
a pump configured to circulate the cooled liquid between the cooling chamber and the reservoir of the dressing and configured to create suction to the suction element to the drain hose; and
a pump valve for modulating suction to the drain hose and to the cooling hose, and
circulating the chilled liquid from the cooling chamber to the reservoir of the dressing.

20. The method of claim 19, further comprising applying negative pressure at, or proximate to, the suction element to remove wound drainage or sweat.

21. The method of claim 19, wherein the method rejuvenates facial skin of the subject.

\* \* \* \* \*